(12) United States Patent
Gupta et al.

(10) Patent No.: US 11,820,764 B2
(45) Date of Patent: Nov. 21, 2023

(54) COMPOUND MODULATING GSK-3 ACTIVITY

(71) Applicant: National Institute of Immunology, New Delhi (IN)

(72) Inventors: Sarika Gupta, New Delhi (IN); Ibrar Ahmed Siddiqui, New Delhi (IN); Aishwarya Nilakhe, New Delhi (IN); Prabhat Upadhyay, New Delhi (IN)

(73) Assignee: National Institute of Immunology, New Delhi (IN)

( * ) Notice: Subject to any disclaimer, the term of this patent is extended or adjusted under 35 U.S.C. 154(b) by 0 days.

(21) Appl. No.: 17/463,717

(22) Filed: Sep. 1, 2021

(65) Prior Publication Data
US 2022/0185805 A1    Jun. 16, 2022

(30) Foreign Application Priority Data

Dec. 15, 2020 (IN) .............................. 202011054435

(51) Int. Cl.
*C07D 417/06* (2006.01)
*A61P 25/28* (2006.01)

(52) U.S. Cl.
CPC ............ *C07D 417/06* (2013.01); *A61P 25/28* (2018.01)

(58) Field of Classification Search
CPC .............................. C07D 417/06; A61P 25/28
See application file for complete search history.

(56) References Cited

U.S. PATENT DOCUMENTS

2010/0190832 A1 *   7/2010   Surolia .................. A61K 31/11
                                                               514/567

* cited by examiner

*Primary Examiner* — Timothy R Rozof
(74) *Attorney, Agent, or Firm* — BakerHostetler

(57) ABSTRACT

The present invention provides a novel compound of formula I, its derivatives, pharmaceutically acceptable salts thereof, and pharmaceutical compositions thereof. Compounds of the present invention are useful for modulating GSK3 level (e.g., GSK3 (e.g., GSK3a/GSK3b or GSK3P) or CK1) hence, activity.

2 Claims, 11 Drawing Sheets

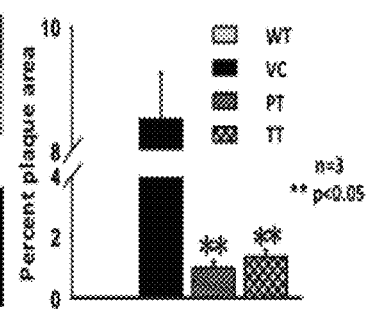

COMPOUND MODULATING GSK-3 ACTIVITY

FIELD OF INVENTION

Figure 1A:
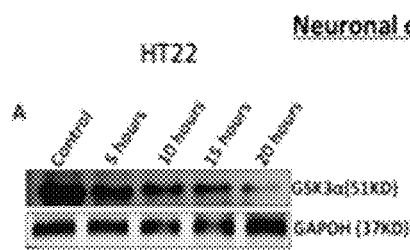

The present invention provides novel compounds of formula I, its derivatives, pharmaceutically acceptable salts thereof, and pharmaceutical compositions thereof. Compounds of the present invention are useful for modulating GSK3 level (e.g., GSK3 (e.g., GSK3a/GSK3b or GSK3P) or CK1) hence, activity.

The present invention further provides methods of using the compounds described herein for treating or preventing GSK3 kinase-mediated disorders, such as neurological diseases: neurodegenerative diseases eg Alzheimer's disease, parkinson's, multiple sclerosis and prion diseases, bipolar disorder and schizophrenia, psychiatric disorders, metabolic disorders: diabetes, gut microbiome disbiosys, cardiovascular, bone and dental diseases, cancer, inflammatory diseases, innate immune response against pathogens and in regenerative stem cell therapy.

BACKGROUND OF INVENTION

The discovery for new therapeutic agents has been immensely aided in recent years by better understanding of the regulation of enzymes and other biomolecules associated with the target diseases. These enzymes and biomolecules regulate key signalling events involve disease pathogenesis. One such important class of enzymes that has been the subject of extensive study is the protein kinases. Many diseases are linked with anomalous cellular responses triggered by these protein kinase-mediated events. These diseases include chronic diseases, autoimmune diseases, inflammatory diseases, neurological and neurodegenerative diseases, cancer, cardiovascular diseases, allergies and asthma, Alzheimer's disease or hormone-related diseases. Therefore, there has been a substantial effort in medicinal chemistry to find protein kinase inhibitors that are effective as therapeutic agents. However, all such efforts are unsuccessful due to toxicity or off-target effect of these inhibitors. Thus method of regulation of such protein kinases either by small molecule or biomolecules would be a healthier approach Glycogen synthase kinase-3 (GSK-3) is a serine/threonine protein kinase having a monomeric structure and a size of approximately 47 kilodaltons. It is one of several protein kinases which phosphorylate glycogen synthase (Embi et al., Eur. J. Biochem. 107:519-527 (1980); Hemmings et al., Eur. J. Biochem. 119:443-451 (1982)). GSK-3 is also referred to in the literature as factor A (FA) in the context of its ability to regulate FC, a protein phosphatase (Vandenheede et al., J. Biol. Chem. 255:11768-11774 (1980)). Other names for GSK-3 and homologs thereof include: zeste-white3/shaggy (zw3/sgg; the *Drosophila melanogaster* homolog), ATP-citrate lyase kinase (ACLK or MFPK; Ramakrishna et al., Biochem. 28:856-860 (1989); Ramakrishna et al., J. Biol. Chem. 260:12280-12286 (1985), GSKA (the Dictyostelum homolog; Harwood et al., Cell 80:139-48 (1995), and MDSI, MCK1, and others (yeast homologs; Hunter et al., TIBS 22:18-22 (1997)), tau protein kinase (mammalian) and GSKA (Dictyostelium).

The gene encoding GSK-3 is highly conserved across diverse phyla. In vertebrates, GSK-3 exists in two isoforms, designated GSK-3α (51 kDa) and GSK-3β (47 kDa). These two isoforms are the products of distinct genes. The amino acid identity among vertebrate homologs of GSK-3 is in excess of 98% within the catalytic domain (Plyte et al., Biochim. Biophys. Acta 1114:147-162 (1992)), although GSK-3α is known to be slightly larger than GSK-3β.

Sun et al., J. Biol. Chem. 277(14):11933-11940 (April 2002) have reported that in brain extracts and in MAP fractions, the amounts of GSK-3α and GSK-3β are almost equal, but that there are profound differences between the amounts of each kinase complexed with tau, further distinguishing the functions of the two. The authors determined that 6-fold more tau is complexed with GSK-3β than with GSK-3α in the brain, and that GSK-3β is bound to tau within an approximately 400-kDa micro-tubule-associated complex. Thus, GSK-3β associates with the microtubules via tau.

GSK-3 phosphorylates numerous proteins in vitro, including beta-catenin, glycogen synthase, phosphatase inhibitor I-2, the type-II subunit of cAMP-dependent protein kinase, the G-subunit of phosphatase-1, ATP-citrate lyase, acetyl coenzyme A carboxylase, myelin basic protein, a microtubule-associated protein, a neurofilament protein, an N-CAM cell adhesion molecule, nerve growth factor receptor, c-Jun transcription factor, JunD transcription factor, c-Myb transcription factor, c-Myc transcription factor, L-myc transcription factor, adenomatous polyposis coli tumor suppressor protein, and tau protein (Plyte et al., 1992; Korinek et al., Science 275:1784-1787 (1997); Miller et al., Genes & Dev. 10:2527-2539 (1996)). The phosphorylation site recognized by GSK-3 has been determined in several of these proteins (Plyte et al., 1992). The diversity of these proteins suggests a wide role for GSK-3 in the control of cellular metabolism, regulation, growth, and development. GSK-3 tends to phosphorylate serine and threonine residues in a proline-rich environment, but does not display the absolute dependence upon these amino acids which is displayed by protein kinases which are members of the mitogen-activated protein (MAP) kinase or cdc2 families of kinases.

Glycogen synthase kinase 3 (GSK-3) is a constitutively active, ubiquitous expressed ser/thr kinase that is involved in a enormous number of signaling pathways. GSK-3 is a key target of a remarkably huge number of cellular processes and diseases such as diabetes type II, cancer, immune disorder, neurodegenerative pathologies among others diseases and surely in regenerative medicine. For decades the scientific community has been working to understand the role of GSK-3 with the aim to design efficient and selectivity GSK-3 inhibitors. However, so far preclinical and clinical GSK3 inhibitors have shown sub-optimal potency, poor GSK-3 selectivity over other CNS targets and closely related kinases, low CNS exposure, and chronic toxicity.

The specificity of GSK-3 inhibitors to cancer are still under intense investigation. The different studies show that GSK-3 are involved in numerous cellular processes being crucial in autophagy regulation and cell-fate mediators (Mancinelli R, Oxid Med Cell Longevity;4629495-4629509 (2017)). Sato N et al, Nat Med; 10(1):55-63,(2004) shown the enhanced self-renewal of both mouse Embryonic stem cells (mESC) and human ESCs (hESCs) employing the GSK-3 inhibitor, as a surrogate activator of Wnt signaling a great number of researches have been performed such as central nervous system (CNS) or in cardiac regeneration (Singh A P, Cardiovasc Res. 115(1):20-30(2019)) but there is still much to investigate. Although, the immune system modulation by GSK-3 is not a new application, more research is needed to understand the role of GSK-3 and the effects of its inhibitors. Sengupta et al; Cancer Lett. 433: 131-139 (2018) reported the adjuvant-like effects of GSK-3 inhibition on activate CAR-T cells could be a successful implementation of CAR-T immunotherapy against GBM and another solid tumor.

Alzheimer's disease (AD) is a neurodegenerative disorder defined by progressive memory loss and cognitive impairment and at the molecular level by the presence of neurofibrillary tangles (NFTs) and insoluble b-amyloid (Ab) plaques (Hardy 2006) that are associated with activated microglia (Vehmas et al. 2003). NFTs are composed of hyper-phosphorylated forms of the microtubule-associated protein tau, whereas Ab is derived from the proteolytic cleavage of b-amyloid precursor protein (APP).

Alzheimer's disease is associated with aberrant processing of the amyloid precursor protein (APP), leading to increased production and aggregation of amyloid-β (Aβ) peptides. Amyloid plaques are composed primarily of 40 and 42 amino acid peptides (Aβ40 and Aβ42, respectively) (Selkoe, Proc. Nat'l. Acad. Sci. USA 98:11039-11041 (2001)) derived from APP by sequential proteolysis catalyzed by the aspartyl protease, BACE (Vassar et al., Science 286:735-741 (1999)), followed by presenilin-dependent γ-secretase cleavage (De Strooper et al., Nature 391:387-390 (1998)). Aβ42 is less soluble than Aβ40 and is the predominant Aβ species in amyloid plaques (Iwatsubo et al., Neuron 13:45-53 (1994)).

Presenilins 1 and 2 (PS1 and PS2) are integral membrane proteins proposed to have inherent γ-secretase activity (Wolfe et al., Nature 398:513-517 (1999)) and interact in a functional complex with nicastrin (Ester et al., Proc. Nat'l. Acad. Sci. USA 99:2720-2725 (2002); Edbauer et al., Proc. Nat'l. Acad. Sci. USA 99:8666-8671 (2002)), aph-1, and pen-2 (Francis et al., Dev. Cell 3:85-97 (2002)). Presenilins also interact with a number of other proteins, including α-catenin and β-catenin (Soriano et al., J. Cell Biol. 152: 785-794 (2001); Yu et al., Nature 407:48-54 (2000)). Presenilin 1, which is required for γ-secretase mediated processing of APP (De Strooper et al., 1998), interacts with glycogen synthase kinase-3 (GSK-3) (Takashima et al., Proc. Nat'l. Acad. Sci. USA 95:9637-9641 (1998); Kang et al., J. Neurosci. 19:4229-4237 (1999); Kang et al., Cell 110:751-762 (2002)), although a functional role for this proteins in γ-secretase function has not been previously established.

Abnormal GSK3 activity is central to many chronic, infectious and inflammatory diseases, hence extensively used as target. Till now various molecules have been reported that can inhibit GSK3 activities. However, such compounds failed in clinical studies due to toxicity, less efficacy or off-target activity. Hence, other ways of modulating GSK3 activity is needed urgently. One such way could be to downregulate GSK3. Downregulating the GSK3 by siRNA have shown preventive and therapeutic effect in chronic diseases including, neurodegenerative disease, metabolic disorders, cancer and inflammatory and infectious disease. This indicates that modulating/regulating GSK3 protein level could be a better strategy than developing inhibitors. Any molecule/protein that can downregulate GSK3 protein level will not only be of great business interest but also improve quality of life and decrease socio-economic burden of the family and this is unmet till now. Therefore there is still a need to find good cellular GSK-3 activity regulator, being both effective and selective, and having good 'drugability properties, i.e. good pharmaceutical properties related to administration, distribution and metabolism. An added advantage would be to find compounds with simple, stable structures, being easy to be prepared by proceedings known to the skilled person.

The present invention provides novel compounds of formula I, its derivatives pharmaceutically acceptable salts thereof, and pharmaceutical compositions thereof. Compounds of the present invention are useful for modulating GSK3 level (e.g., GSK3 (e.g., GSK3α/GSK3β or GSK3P) or CK1) hence, activity. In particular, the compounds of formula I induces downregulation of GSK3 (both α&β) in vivo and in situ and induces autophagy pathway. The compounds of formula I improve spacial memory, exploratory behavioural, working memory and alleviate behavioural deficit in Alzheimer's mice via downregulating GSK3 and inducing autophagy degradation pathways.

The present invention further provides methods of using the compounds described herein for treating or preventing GSK3 kinase-mediated disorders, such as neurological diseases such as Alzheimer's disease, psychiatric disorders, metabolic disorders, and cancer.

SUMMARY OF INVENTION

The present invention provides novel compounds of formula I, its derivatives or pharmaceutically acceptable salts thereof that modulate GSK3 level (e.g., GSK3 (e.g., GSK3a/GSK3b or GSK3P) or CK1) hence, activity. In particular, the compounds of formula I induces down-regulation of GSK in vivo and in situ and induces autophagy pathway. The inventors have chosen alzheimers disease, a GSK3 related disease as an example to prove the concept. The compounds of formula I improve spacial and working memory and alleviate behavioural deficit in Alzheimer's mice via down-regulating GSK3 and inducing autophagy degradation pathways.

In one aspect, the present invention refers to novel compound 6-(5-ethylidene-4-oxo-2thioxo-thiazolidin-3-yl)-hexanoic acid with 1H-indole of formula I,

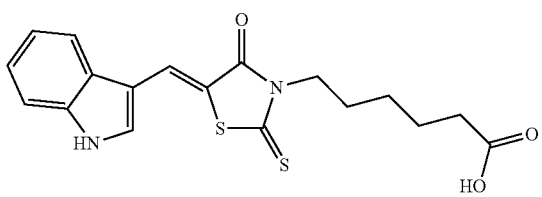 [SMILES: O=C(O)CCCCCN1C(=O)/C(=C/c2c[nH]c3ccccc23)SC1=S]

its derivatives, or pharmaceutically acceptable salts.

In a further aspect, the present invention relates to a compound for use in treating or preventing a GSK-3 mediated disease/disorders wherein the compound is 6-(5-ethylidene-4-oxo-2thioxo-thiazolid in-3-yl)-hexanoic acid compound with 1H-indole of formula I

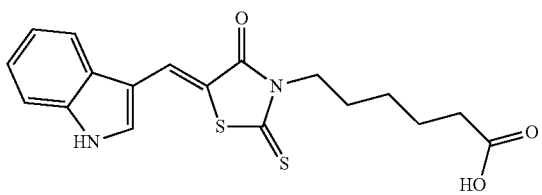 [SMILES: O=C(O)CCCCCN1C(=O)/C(=C/c2c[nH]c3ccccc23)SC1=S]

its derivatives, or pharmaceutically acceptable salts.

In yet another aspect, the present invention relates to pharmaceutical composition comprising an effective amount of compound of formula I, its derivatives, or a pharmaceutically acceptable salt thereof along with a pharmaceutically acceptable excipients, carriers or diluents.

One or more aspect of the present invention relates to compound 6-(5-ethylidene-4-oxo-2thioxo-thiazolidin-3-yl)-hexanoic acid compound with 1H-indole of formula I, its derivatives, or a pharmaceutically acceptable salt thereof, for use and in the manufacture of a medicament for treating or preventing a GSK-3 mediated disease/disorders.

In another aspect, the GSK-3 mediated disease is selected from chronic neurodegenerative disease such as Alzheimer's disease, psychiatric disorders, metabolic disorders, and cancer.

In one aspect, the present invention relates to a process of preparation of pharmaceutical composition, comprising the step of mixing an effective amount of compound 6-(5-ethylidene-4-oxo-2thioxo-thiazolidin-3-yl)-hexanoic acid compound with 1H-indole of formula I, its derivatives, or a pharmaceutically acceptable salt thereof along with a pharmaceutically acceptable excipients, carriers or diluents In yet another aspect, the present invention relates to a method of treating or preventing the GSK-3 mediated disease/disorder, comprising the administration of the compound 6-(5-ethylidene-4-oxo-2thioxo-thiazolidin-3-yl)-hexanoic acid compound with 1H-indole of formula I to a subject.

In another aspect, the present invention relates to a method of treating or preventing the GSK-3 mediated disease/disorder, comprising the administration of the pharmaceutical composition comprising an effective amount of compound of formula I, its derivatives, or a pharmaceutically acceptable salt thereof along with a pharmaceutically acceptable excipients, carriers or diluents to a subject.

In a further aspect, the present invention provides a kit for treating or preventing the GSK-3 mediated disease/disorder comprising a compound 6-(5-ethylidene-4-oxo-2thioxo-thiazolidin-3-yl)-hexanoic acid compound with 1H-indole of formula I, its derivatives, or a pharmaceutically acceptable salt thereof, pharmaceutically acceptable excipients, carriers or diluents and a set of instructions on how to use said kit.

One or more aspect of the present invention relates to 6-(5-ethylidene-4-oxo-2thioxo-thiazolidin-3-yl)-hexanoic acid compound with 1H-indole of formula I, its derivatives, or a pharmaceutically acceptable salt thereof, for use and in the manufacture of a medicament for Regenerative medicine.

DRAWINGS

Figure 1B:
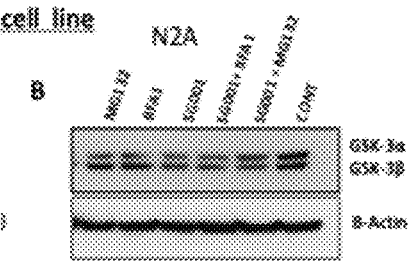
Figure 1C:
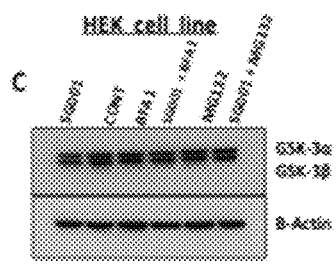
Figure 1D:
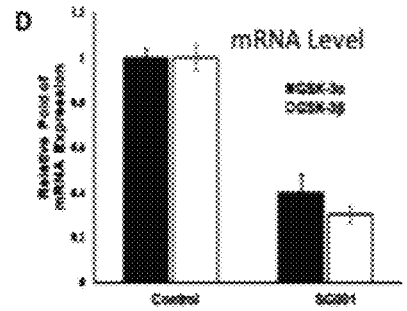
Figure 2A:
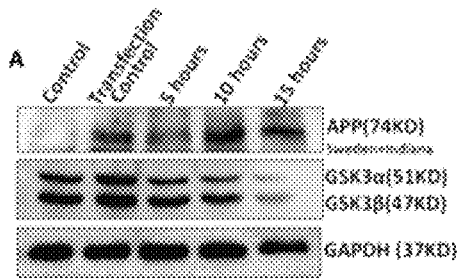
Figure 2B:
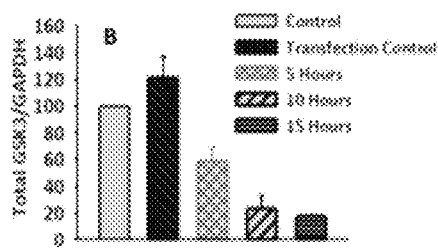
Figure 3A:
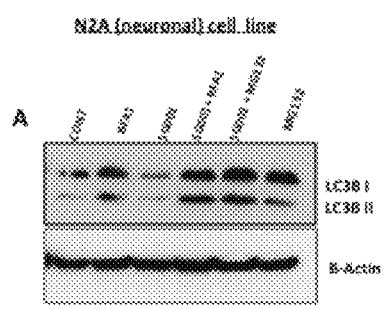
Figure 3B:
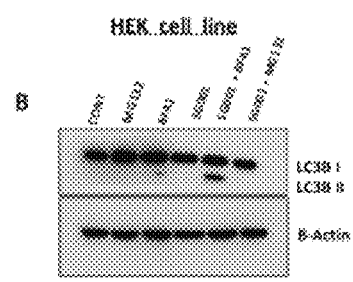
Figure 3C:
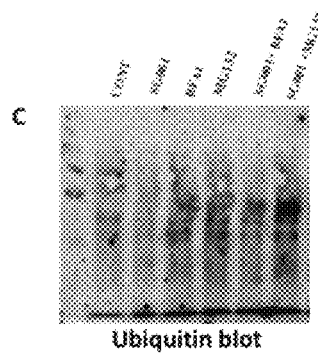
Figure 4A:
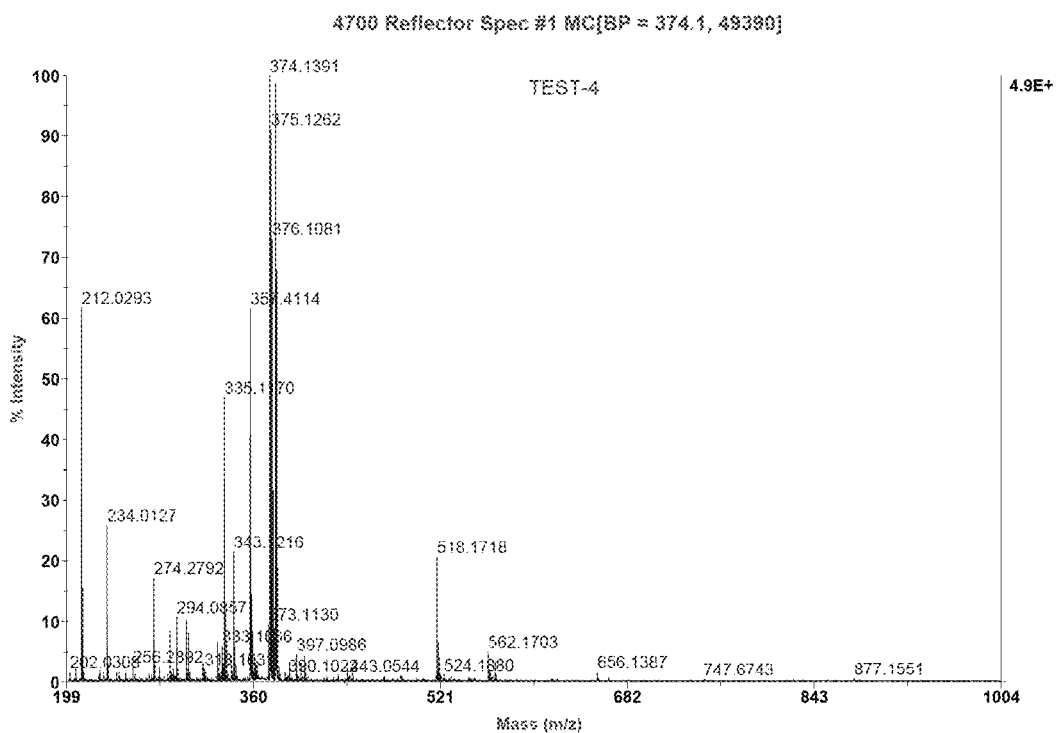
Figure 4B:
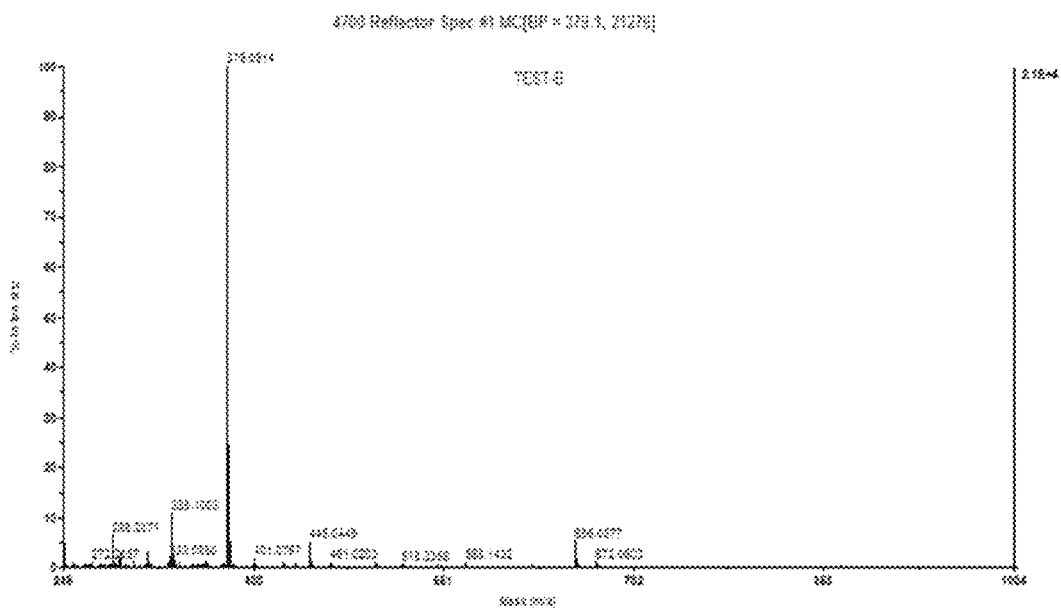
Figure 4C:
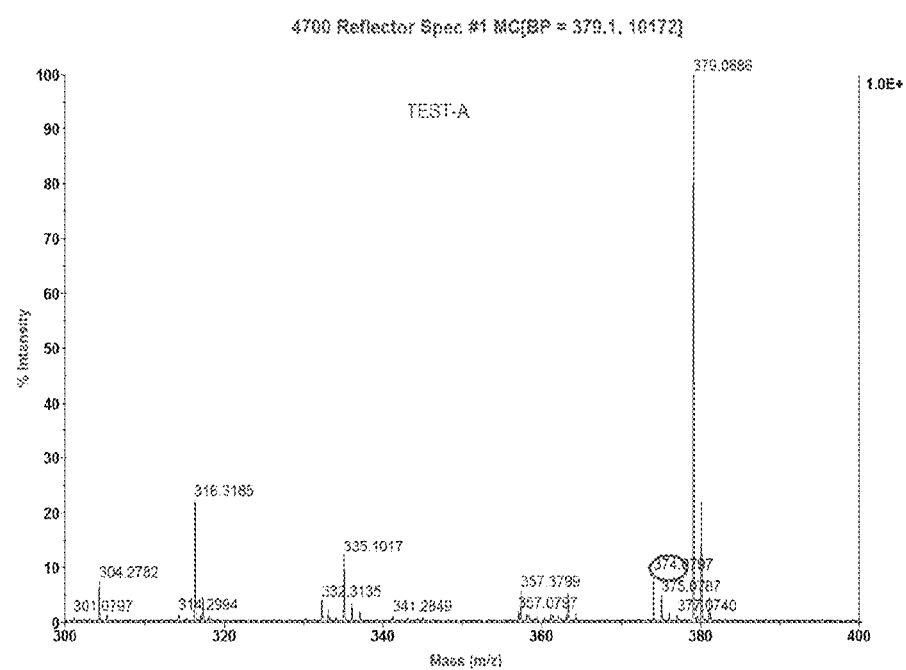
Figure 5:
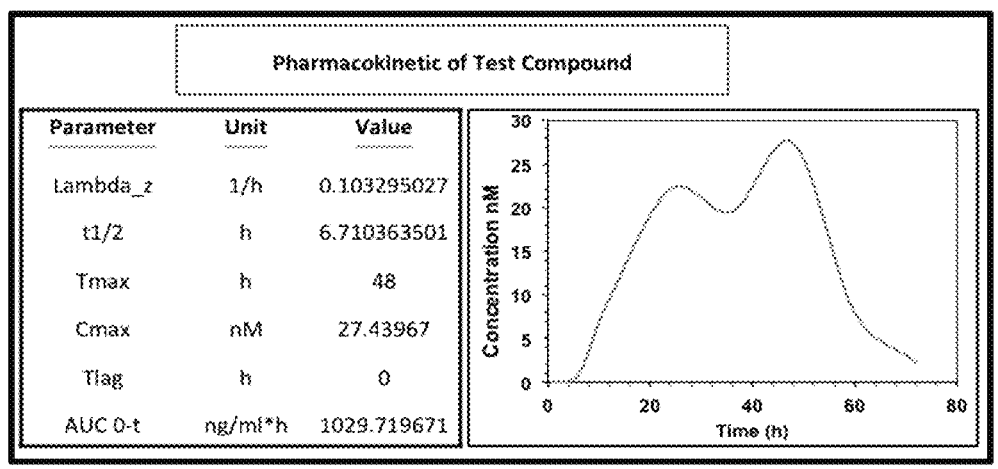
Figure 6:
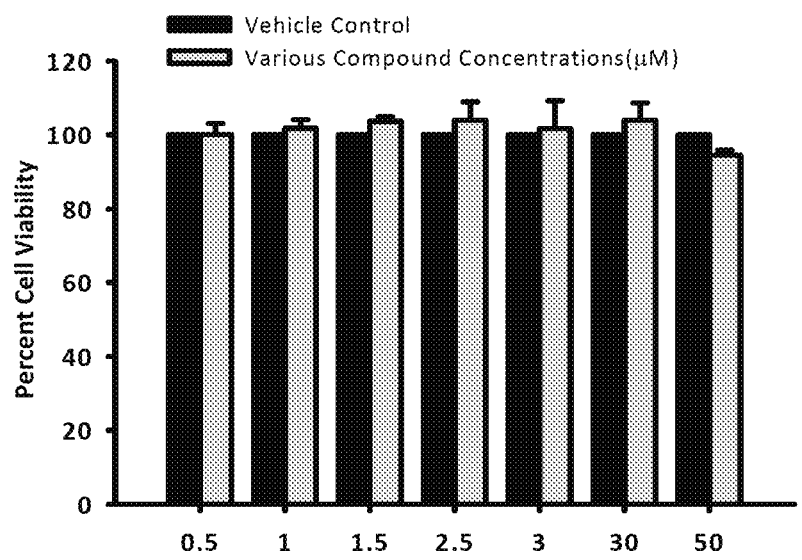
Figures 7A, 7B, 7C:
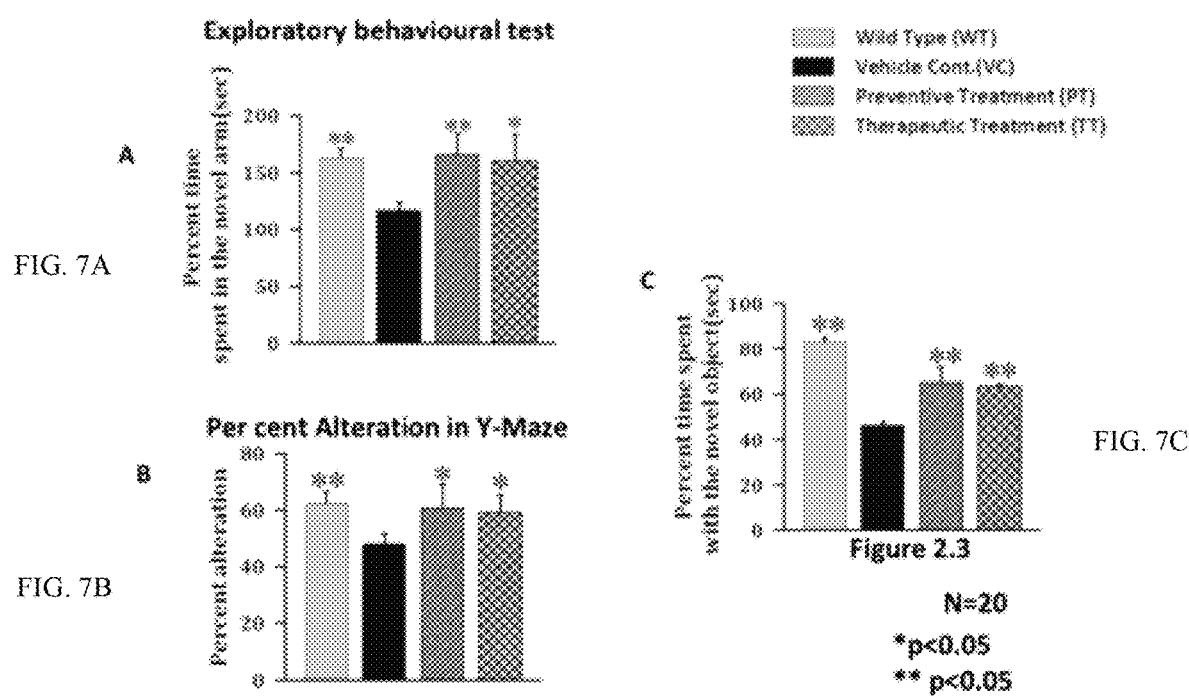
Figure 8A:
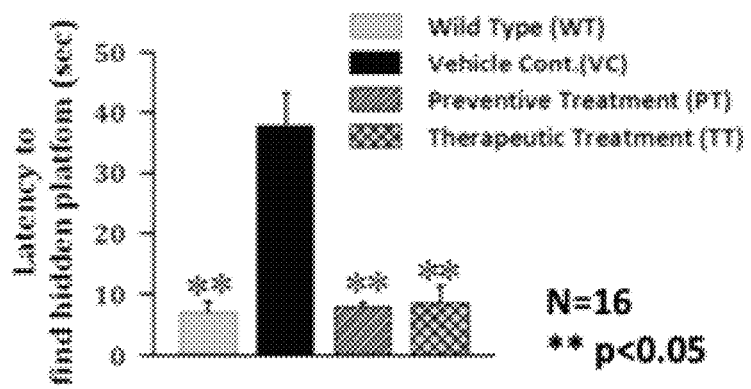
Figure 8B:
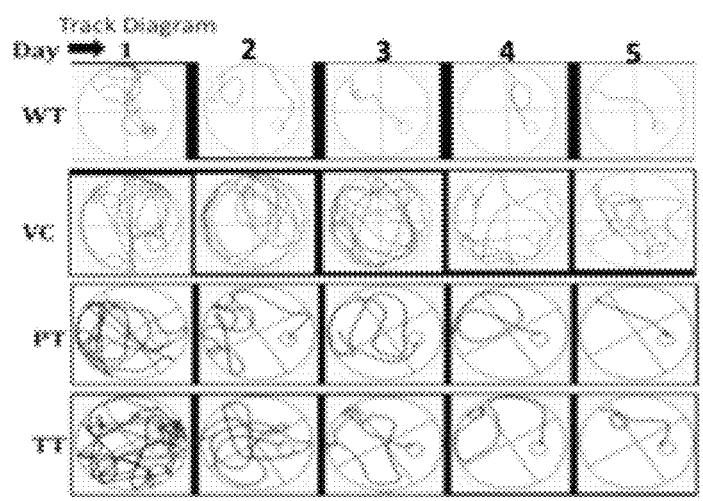

The foregoing summary, as well as the following detailed description of the invention will be better understood when read in conjunction with the appended drawings. For the purpose of assisting in the explanation of the invention, these are shown in the drawings embodiments which are presently preferred and considered illustrative. It should be understood, however, that the invention is not limited to the precise arrangements and instrumentalities shown therein. In the drawings:

FIGS. 1A, 1B, 1C and 1D graphically illustrate downregulation of GSK3 in time dependent manners in neuronal and non-neuronal cell lines, particularly FIG. 1A is for HT22; FIG. 1B is for N2A; FIG. 1C is for HEK cell line; and FIG. 1D is for mRNA Level;

FIGS. 2A-2B: Graphs illustrating the down regulation of GSK3 in cellular model of AD (APP (Sweden+Indiana) overexpressing HT-22, hippocampal cell line) upon SG001 treatment; FIG. 2A Immunoblot analysis using anti-GSK3a&b antibody, FIG. 2B Densitometric analysis of immunoblot;

FIG. 3: Illustrates the induction of cellular degradatory pathways by SG001;

FIG. 4: Graph demonstrating that the compound crosses the blood brain barrier, mass spectrometry analysis of cerebrospinal fluid from control and SG001 treated mice;

FIG. 5: Demonstrates the pharmacokinetics of the compound SG001;

FIG. 6: Graphs illustrating the Cell cytotoxicity assay;

FIGS. 7A-7C: Graphs illustrating the results of behavioural assessments of the 5× FAD mouse after the Sg001 preventive and therapeutic treatments: FIG. 7A Exploratory behaviour test FIG. 7B Percent alteration in the Y-Maze FIG. 7C Novel object test;

FIG. 8A-8B: Graph illustrating behavioural assessments of the 5× FAD mouse after the SG001 preventive and therapeutic treatments using Morris water maze(MWM);

FIG. 8A showing Escape latency and FIG. 8B track diagram of MWM.

Figure 9A:
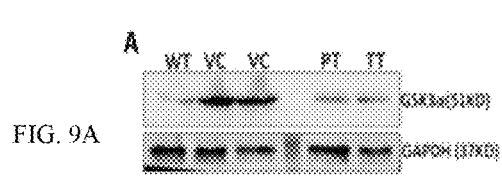

FIGS. 9A-9D: Result showing that compound contributes in the ameliorated AD pathology vide GSK3 downregulation and induction of GSK regulated autophagy pathway; FIG. 9A level of GSK3 in brain hippocampus lysate, FIG. 9B immunohistochemistry of GSK3 in brain tissue section, FIG. 9C Fold change in the GSK3 mRNA level in hippocampus lysate, FIG. 9D immunofluorescence of LC3BII in the brain section.

Figure 10A:
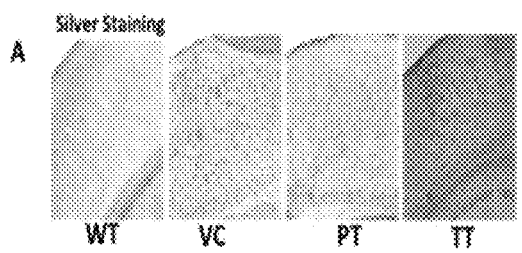
Figure 10B:
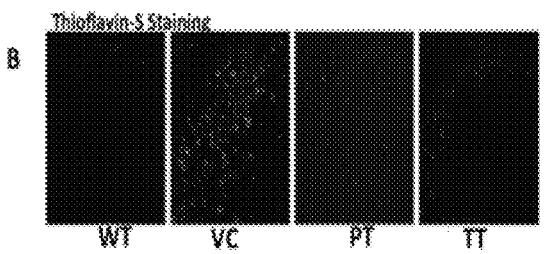
Figure 10C:
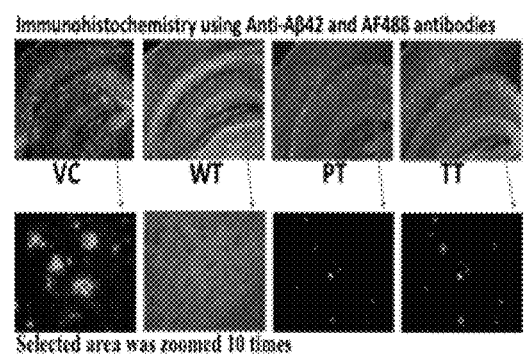
Figure 10D:
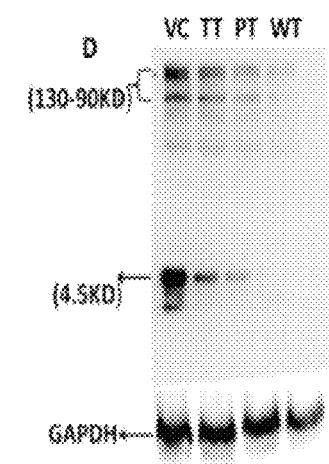

FIGS. 10A-10D: Graph demonstrating the histopathological analysis of SG001 treated 5× FAD animals: FIG. 10A Silver staining of the cortex region of the animal's brain sections showing the significant decrease in the amyloid like plaque in the SG001 treated animals; FIG. 10B Thioflavin-S staining showing the significant decrease in the amyloid plaque in the hippocampus region of the SG001 treated animal brains, when compared with the vehicle control; FIG. 10C Upper panel showing the immunohistochemistry for the Aβ42 of the brain sections focusing the cortex and the hippocampus area, a drastic decrease in the frequency of the Aβ42 plaque in the SG001 treated animals were observed. Lower panel is zoomed four times and showing the drastic decrease in the size of the plaque in the SG001 treated animals; FIG. 10D Tricine-Gel electrophoresis of the total brain homogenate showing the significant decrease in the total(soluble+aggregated) Aβ42 level in the SG001 treated animal's brain.

Figure 11A:
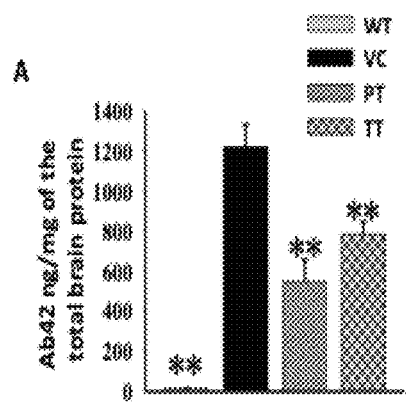
Figure 11B:
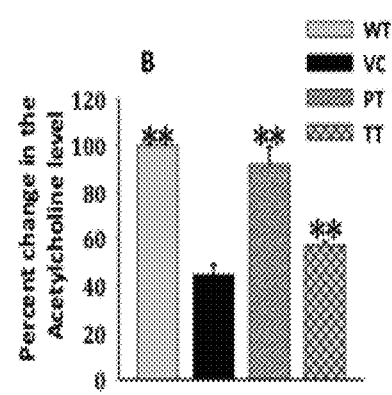
Figure 11C:
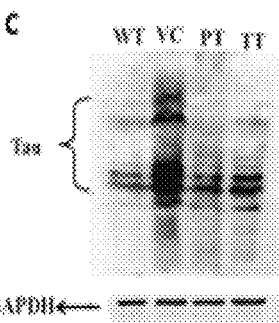
Figure 11D:
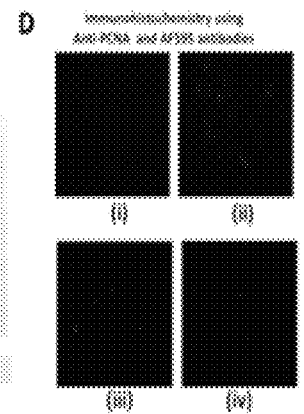
Figure 11E:
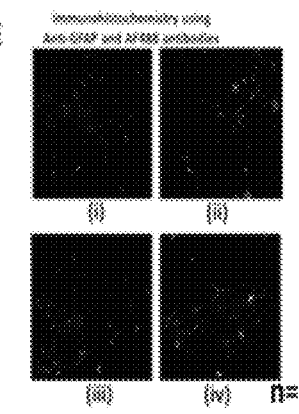

FIGS. 11A-11E: Graph demonstrating the acetylcholine level in the brain of compound treated animals. FIG. 11A Sandwich ELISA showing the quantitative analysis for the total Aβ42 levels in the brains of the animals. The SG001 treatment resulted in the significant decrease in the level of the total Aβ42 levels. FIG. 11B Level of neurotransmitter acetylcholine was checked and found restored significantly in the SG001 treated animals. FIG. 11C Immunoblot for the total Tau level in the brain of the SG001 animals. Vehicle control animals shows the higher molecular weight Tau-aggregates, while less aggregates and the low level of the Tau protein was detected in the SG001 treated animals. FIG. 11D Immunohistochemistry of the brain sections for the PCNA shows the inflammation in the brain. The inflammation was reduced after the treatment of the animals. FIG. 11E The immunohistochemistry of the GFAP protein was done of the brain sections, which shows the morphology of the astrocytes. The morphology of the astrocytes were found distorted in the diseased control(VC) animals, while the morphology was restored in the treated animals.

Figure 12:
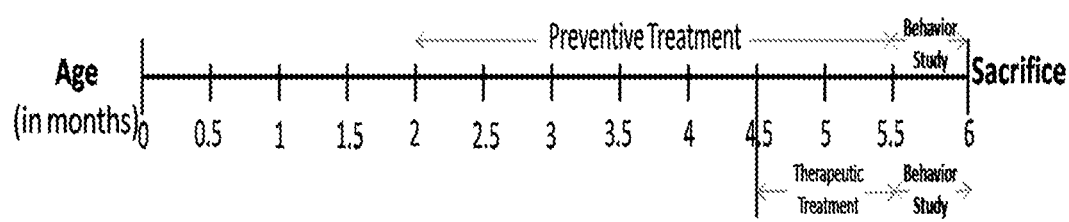

FIG. 12 depicts a timeline for preventive treatment of sample mice.

DETAILED DESCRIPTION OF INVENTION

In describing the invention, the following terminology will be used in accordance with the definitions set forth below. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein. As used herein, each of the following terms has the meaning associated with it in this section. Specific and preferred values listed below for individual process parameters, substituents, and ranges are for illustration only; they do not exclude other defined values or other values falling within the preferred defined ranges.

As used herein, the singular forms "a," "an," and "the" include plural reference unless the context clearly dictates otherwise.

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

When the term "about" is used in describing a value or an endpoint of a range, the disclosure should be understood to include both the specific value and endpoint referred to.

As used herein, the terms "comprising" "including," "having," "containing," "involving," and the like are to be understood to be open-ended, i.e. to mean including but not limited to.

As used herein, the term "pharmaceutically acceptable" means a compound which is suitable for pharmaceutical use. Salts and solvates of compounds of the invention which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of the invention and their pharmaceutically acceptable salts and solvates.

As used herein, the term "pharmaceutically acceptable salts" means pharmaceutically acceptable salts that are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid.

Any conventional carrier or excipient may be used in the pharmaceutical compositions of this invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts.

Representative examples of materials which can serve as pharmaceutically acceptable carriers include, but are not limited to, the following: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) compressed propellant gases, such as chlorofluorocarbons and hydrofluorocarbons; and (22) other non-toxic compatible substances employed in pharmaceutical compositions.

As used herein, the term "pharmaceutical composition" comprises an effective amount of compounds of formula I, or a pharmaceutically acceptable salt thereof along with a pharmaceutically acceptable excipients, carriers or diluents. Such pharmaceutical compositions may be administered to the patient by any acceptable route of administration including, but not limited to, inhaled, oral, nasal, topical (including transdermal) and parenteral modes of administration, in particular inhaled administration.

The present invention provides novel compound 6-(5-ethylidene-4-oxo-2thioxo-thiazolidin-3-yl)-hexanoic acid compound with 1H-indole of formula I, its derivatives, or pharmaceutically acceptable salts thereof that modulate GSK3 level (e.g., GSK3 (e.g., GSK3a/GSK3b or GSK3P) or CK1) hence, activity. In particular, the compounds of formula I induces degradation of GSK in vivo and in situ via autophagy dependent pathway. The compound of formula I improve behavioural and memory deficit in Alzheimer's mice via autophagy dependent GSK3 degradation.

In an embodiment, the present invention refers to novel compound 6-(5-ethylidene-4-oxo-2thioxo-thiazolidin-3-yl)-hexanoic acid compound with 1H-indole of formula I

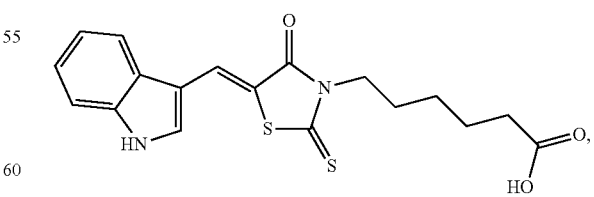

its derivatives or pharmaceutically acceptable salts.

In a further embodiment, some of the derivatives of compounds of formula I but not limited to is as follows:

| SNO | STRUCTURE | NAME |
|---|---|---|
| 1 | 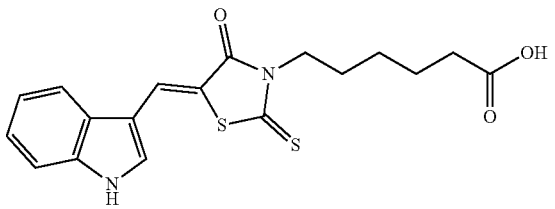 | (Z)-6-(5-((1H-indol-3-yl)methylene)-4-oxo-2-thioxothiazolidin-3-yl)hexanoic acid |
| 2 | 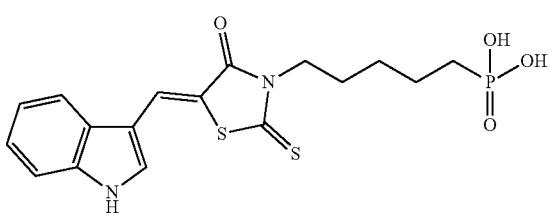 [SMILES: O=C1/C(=C/c2c[nH]c3ccccc23)SC(=S)N1CCCCCP(=O)(O)O] | (Z)-(5-(5-((1H-indol-3-yl)methylene)-4-oxo-2-thioxothiazolidin-3-yl)pentyl) phosphonic acid |
| 3 | 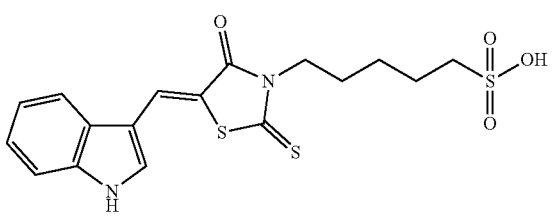 [SMILES: O=C1/C(=C/c2c[nH]c3ccccc23)SC(=S)N1CCCCCS(=O)(=O)O] | (Z)-5-(5-((1H-indol-3-yl)methylene)-4-oxo-2-thioxothiazolidin-3-yl)pentane-1-sulfonic acid |
| 4 | 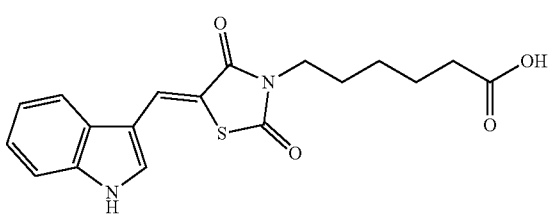 | (Z)-6-(5-((1H-indol-3-yl)methylene)-2,4-dioxothiazolidin-3-yl)hexanoic acid |
| 5 | 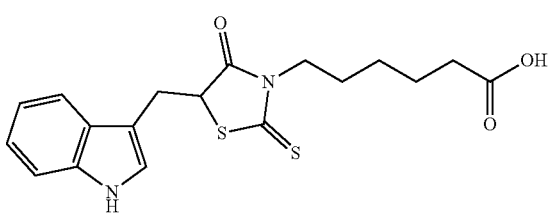 [SMILES: O=C(O)CCCCCN1C(=O)C(Cc2c[nH]c3ccccc23)SC1=S] | 6-(5-((1H-indol-3-yl)methyl)-4-oxo-2-thioxothiazolidin-3-yl)hexanoic acid |
| 6 | 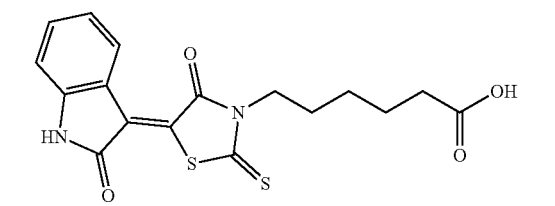 [SMILES: O=C(O)CCCCCN1C(=O)/C(=C2/C(=O)Nc3ccccc32)SC1=S] | (Z)-6-(4-oxo-5-(2-oxoindolin-3-ylidene)-2-thioxothiazolidin-3-yl)hexanoic acid |
| 7 | 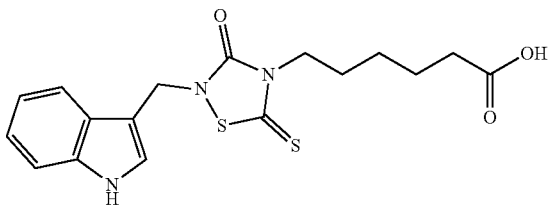 [SMILES: O=C(O)CCCCCn1c(=S)sn(Cc2c[nH]c3ccccc23)c1=O] | 6-(2-((1H-indol-3-yl)methyl)-3-oxo-5-thioxo-1,2,4-thiadiazolidin-4-yl)hexanoic acid |

-continued

| SNO | STRUCTURE | NAME |
|---|---|---|
| 8 | 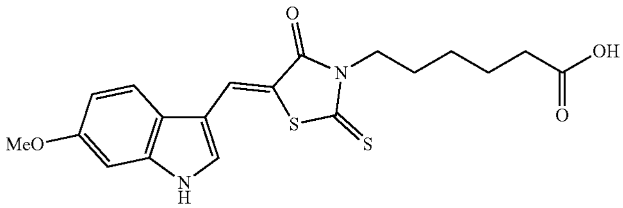 [SMILES: COc1ccc2c(/C=C3\SC(=S)N(CCCCCC(=O)O)C3=O)c[nH]c2c1] | (Z)-6-(5-((6-methoxy-1H-indol-3-yl)methylene)-4-oxo-2-thioxothiazolidin-3-yl)hexanoic acid |
| 9 | 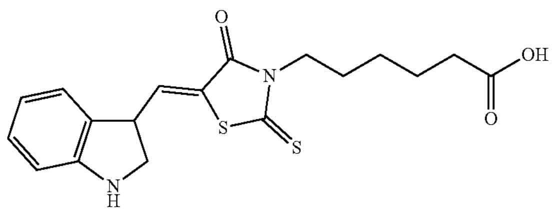 [SMILES: O=C(O)CCCCCN1C(=O)/C(=C/C2CNc3ccccc32)SC1=S] | (Z)-6-(5-(indolin-3-ylmethylene)-4-oxo-2-thioxothiazolidin-3-yl)hexanoic acid |
| 10 | 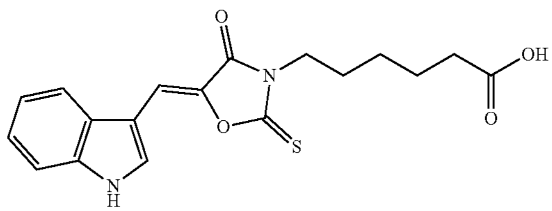 [SMILES: O=C(O)CCCCCN1C(=O)/C(=C/c2c[nH]c3ccccc23)OC1=S] | (Z)-6-(5-((1H-indol-3-yl)methylene)-4-oxo-2-thioxooxazolidin-3-yl)hexanoic acid |
| 11 | 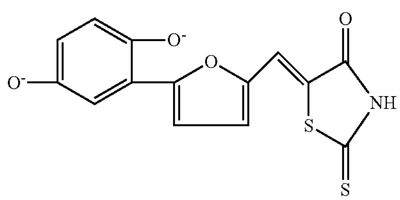 [SMILES: O=C1NC(=S)S/C1=C\c1ccc(-c2cc([O-])ccc2[O-])o1] | 5-[[5-(2,5-dichlorophenyl)furan-2-yl]methylidene]-2-sulfanylidene-1,3-thiazolidin-4-one |

In another embodiment, the present invention relates to a compound for use in treating or preventing a GSK-3 mediated disease/disorders wherein the compound is 6-(5-ethylidene-4-oxo-2thioxo-thiazolidin-3-yl)-hexanoic acid compound with 1H-indole of formula I

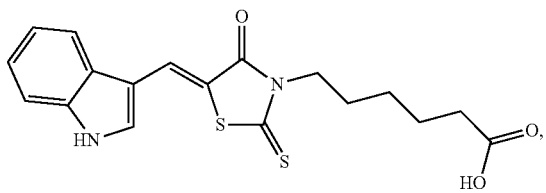 [SMILES: O=C(O)CCCCCN1C(=O)/C(=C/c2c[nH]c3ccccc23)SC1=S]

its derivatives or pharmaceutically acceptable salts.

In yet another embodiment, the present invention relates to pharmaceutical composition comprising an effective amount of compound 6-(5-ethylidene-4-oxo-2thioxo-thiazolidin-3-yl)-hexanoic acid compound with 1H-indole of formula I, its derivatives or a pharmaceutically acceptable salt thereof along with a pharmaceutically acceptable excipients, carriers or diluents.

One or more embodiment of the present invention relates to compound 6-(5-ethylidene-4-oxo-2thioxo-thiazolidin-3-yl)-hexanoic acid compound with 1H-indole of formula I, its derivatives or a pharmaceutically acceptable salt thereof, for use and in the manufacture of a medicament for treating or preventing a GSK-3 mediated disease/disorder.

In another preferred embodiment, the GSK-3 mediated disease/disorder is selected from chronic neurodegenerative disease such as Alzheimer's disease, psychiatric disorders, metabolic disorders, and cancer.

In a further embodiment, the present invention relates to a process of preparation of pharmaceutical composition, comprising the step of mixing an effective amount of compound 6-(5-ethylidene-4-oxo-2thioxo-thiazolidin-3-yl)-hexanoic acid compound with 1H-indole of formula I, its derivatives or a pharmaceutically acceptable salt thereof along with a pharmaceutically acceptable excipients, carriers or diluents.

In yet another embodiment, the present invention relates to a method of treating or preventing the GSK-3 mediated disease, comprising the administration of the compound of formula I to a subject.

In another embodiment, the present invention relates to a method of treating or preventing the GSK-3 mediated disease, comprising the administration of the pharmaceutical composition comprising an effective amount of compound 6-(5-ethylidene-4-oxo-2thioxo-thiazolidin-3-yl)-hexanoic acid compound with 1H-indole of formula I, its derivative or a pharmaceutically acceptable salt thereof along with a pharmaceutically acceptable excipients, carriers or diluents to a subject.

In a yet another embodiment, the present invention provides a kit for treating or preventing the GSK-3 mediated disease/disorder comprising a compound 6-(5-ethylidene-4-oxo-2thioxo-thiazolidin-3-yl)-hexanoic acid compound with 1H-indole of formula I, its derivatives or a pharmaceutically acceptable salt thereof, pharmaceutically acceptable excipients, carriers or diluents and a set of instructions on how to use said kit.

In a yet in another embodiment, the present invention provides composition comprising a compound 6-(5-ethylidene-4-oxo-2thioxo-thiazolidin-3-yl)-hexanoic acid compound with 1H-indole of formula I, its derivatives, or a pharmaceutically acceptable salt thereof, for use and in the manufacture of a medicament for Regenerative medicine.

Although any methods and materials similar or equivalent to those described herein can be used in the practice or testing of the present invention, the preferred methods and materials are described. All publications and other references mentioned herein are incorporated by reference in their entirety. Numeric ranges are inclusive of the numbers defining the range.

The use of examples anywhere in this specification including examples of any terms discussed herein is illustrative only, and in no way limits the scope and meaning of the invention or of any exemplified term. Likewise, the invention is not limited to various embodiments given in this specification.

EXAMPLES

Materials and Methods

Antibodies, Plasmid and Reagents

The pCAX-APP (Swe/Ind) was procured from Addgene (30145, deposited by Dennis Selkoe, Tracy Young-Pearse). Antibodies to Aβ42 peptide (SC-58508), Tau (CST #4019), PCNA (SC-56), GFAP (CST #3670), BACE (CST #5606), PSEN1(AbcamAb76083), EEA1(CST #3288), Neprilysine (SC-46656), pPP2A (SC-12615), LC3BII (CST #2775), RAGE(CST #6996), LRP1 (AbcamAb195567), ApoE (SC-53570), JNK(CST #9252), GSK3α(CST #4818), FAK(CST #3285), ERK(AbcamAb50011), CDK5 (CST #14145), C-Myc (SC-764), Fyn(CST #4023), GSK3(α+β) (CST #5676), APP(CST #2452), Caspase3(CST #9662), CREB(CST #9197), Gelsolin(CST #12953), BAX(SC-6236), GAPDH (SC-47724)

Cell Culture, Transfection, Kits and Treatment

Cell lines used for the study were SH-SY5Y, N2A, HT-22 and HEK 293 procured from ATCC and maintained at the 37° C. in a humidified incubator supplied with the 5% $CO_2$. Dulbecco's modified Eagle medium (DMEM, GIBCO) to which 10% fetal bovine serum (FBS, GIBCO) and 1 mM glutamine were added was used to grow the cells. Lipofectamine LTX plus reagent (Thermo Fisher) was used for the transfection. (SG001) (6-(5-Ethylidene-4-oxo-2thioxo-thiazolidin-3-yl)-Hexanoic acid compound with 1H-indole) was diluted in the low serum media for the cell line treatment. Amyloid Aβ42 human ELISA kit (KHB3441) from Invitrogen, Amplex Acetylcholine/Acetylcholinesterase Assay kit (A12217) from Thermo fisher scientific, DAB enhanced liquid substrate system tetrahydrochloride (D7304).

Animals

B6SJL-Tg(APPSwF1Lon,PSEN1*M146L*L286V) 6799Vas/Mmjax/5× FAD transgenic mice were procured from Jacksons Laboratory. Animals were maintained at the animal house facility of National Institute of Immunology in a controlled temperature of 22±2° C., with a 12 h light/12 h dark cycle and were allowed to access food and water ad libitum. All animal procedures were approved by the Institutional Animal Ethics Committee.

Real Time PCR:

Real Time PCR (qPCR) was performed for analysis of Gsk-3 gene expression in N2a cells treated for 24 h in DMEM in serum deprived condition, in the absence or presence of Bafilomycin A1 (250 nano molar) and compound SG001 (1 ug). The house keeping gene β-Actin was used as the internal control in this study. cDNA was synthesized with a Revert Aid cDNA synthesis kit (Fermentas, Austin, USA) using 1 μg of total RNA. SYBR green chemistry was used to perform the quantitative determination of relative expression of transcripts for all genes. All genes were analyzed using the Light Cycler 480 (Roche Molecular Biochemicals, Indianapolis, Indiana, USA) real time PCR machine.

Western Blot:

Western blotting was performed following routine protocols used in our laboratory. N2a cells treated for 24 h in DMEM in serum deprived condition, in the absence or presence of Bafilomycin A1 (250 nano molar) and compound SG001 (1 aug). The cells then were homogenized with RIPA lysis buffer, and total proteins were quantified by Bradford assay. Aliquots of 40 μg of cell lysates were separated on SDS-PAGE and then transferred to polyvinylidene difluoride (PVDF) membranes (Millipore, Watford, UK). The membranes were incubated with different antibodies, including anti-GSK-3alpha/beta(51, 46 Kda: CST) anti-LC3A/B (14, 16 kDa: CST), anti—JWA(17Kda: Santa Cruz Technologies) and anti β-actin (42 kDa; Santa Cruz Technologies). Western blot signals were detected using the ECL-Plus Western blotting system.

Cytotoxicity Assay

SH-SYSY and HT-22 cells were grown in DMEM media with 10% FBS and anti-anti up to the 70% of the confluence. The compound was added in different dose under the serum starvation condition for 12 hours. MTT([3-(4,5-dimethyl-2-thiazolyl)-2, 5-diphenyl-2 tetrazolium bromide) (Himedia cat no.) was added in a working concentration of 0.5 mg/ml and incubated for 4 hours. Then the cells were observed under the light microscope for the crystal like structure, then DMSO was added to dissolve the crystal and OD was taken at 570 nm using the Tecan. Cell viability was calculated using the formula $C=(A/At)\times 100$, where C is percent cell viability and A and At are the absorbance of treated and untreated samples respectively after subtracting the absorbance of MTT only.

Animal Treatment

FIG. 12 depicts a timeline for preventing treatment of sample mice. All animals were divided into four groups each group having 6 to 8 mice, one group of wild type littermate and other three groups of transgenic mice confirmed by PCR using the specific primers for PSEN and internal control recommended by the Jackson laboratory. All the transgenic animals were divided into three groups: vehicle control, preventive treatment and the therapeutic treatment. The treatment was started at the age of 2 months for the vehicle control and preventive treatment group and for the therapeutic group; the treatment was started at the age of 4.5 months. Intraperitoneal injection of 10 ng/Kg of the body weight was given to the preventive group, while 25 ng/Kg of the body weight was given to the therapeutic group on alternative day's up to the 6 months of the age.

Behavioural Assessments

At the age of 5.5 months, behavioural experiments were started using the Any-maze animal tracking software with the video recording. The persons performing the behavioural experiments were unaware of the treatment groups.

Exploratory Behavioural Test

One of the three identical arms of the Y-Maze was blocked, and animals were allowed to explore the other two open arms for 2 minutes. After this, animals were brought back to their cage for 2 minutes; and meanwhile the maze was cleaned with the 70% ethanol. The animals were taken back to the Y-Maze with all three arms open. The time spent in the novel arm was calculated.

Percent Alteration Test

The animals were allowed to explore all the three arms of the Y-Maze for 8 minutes, and the sequence pattern of the movement was recorded to calculate the percent alteration.

Percent alteration=(No. Of triads/Total number of entries)×100

Where triad is a combination of three different entries of the Y-Maze like ABC, CBA, CAB etc.

Novel Object Test

The animals were left with the two identical objects for the 3 hours, then animals were taken back to their cage for the 2 min and one of the objects was changed meanwhile. After this the animals were allowed to explore both the objects for another 10 minutes and the percent time spent with the novel object was calculated.

Morris Water Maze

The water tank was divided into four quadrants, hidden platform was kept in one of the quadrant and animal was released in the opposite quadrant facing the wall of the tank. The position of the hidden platform and the animal dropping position were constant throughout the experiment. Five days training was given to the animals. On the first day, the animals were kept on the platform for the 15-20 seconds and guided to the platform if could not find it in the 120 seconds. Time taken to find the hidden platform on the final day was plotted.

Animal Sacrifice

At the end of the six months of the age half animals from each group were sacrificed with the perfusion using 4% PFA for the cryosectioning and other halves were sacrificed without perfusion for the homogenate preparation.

Cryosectioning

Brains were harvested by perfusion using 4% ice cold PFA, and passed through the sucrose gradient from 5 to 30% for 6 hours each. Then the tissues were embedded in the polyfreez at −80° C. and coronal sections of 20 micron were cut and taken on the poly-L-lysine coated slides.

Brain Homogenate Preparation

Brain homogenates were made in 0.1M potassium phosphate buffer (pH7.4) containing 0.25M sucrose with protease inhibitors cocktail and phosphatase inhibitor. An aliquot of the total brain homogenate was used for the ELISA. The remaining portion was centrifuged at the 1000 g for 10 minute to get the post-nuclear supernatant this was further centrifuged at 100,000 g for one hour to obtain the cytosolic fraction. Protein concentration was estimated using the Bradford method for all the fractions. The post-nuclear fraction was resolved on the SDS-PAGE and transferred on the PVDF and probed for the BACE, NEP, Presinillin, pPP2A, Gelsolin, LC3B, GSK3α, GSK3β etc with GAPDH as the loading control. The cytosolic fraction was resolved on the 16.5% tricine gel and transferred on the 0.25 μm pore size nitrocellose membrane and probed for the Aβ42.

Silver Staining of the Brain Sections

Bielschowsky silver staining of the brain sections was done to see the amyloid plaque in the cortex region of the brain. Pictures were taken under the light microscope using the 4× lens. Slides were immersed in 4% argent nitrate (AgNO3) for 30 minutes in dark at 37° C. Deoxydized in 10% formaldehyde then incubated with ammonical silver for 5 minutes and further dipped in 8% formalin for 2 minutes. Fixed in 5% sodium thiosulphate for 5 minutes and cleaned in xylene.

Thioflavin-S Staining

ThS staining was done, to see the amyloid load in the hippocampus region of the brain. Pictures were taken under the fluorescence microscope using the FITC filter ai 4× of eyepiece. The sections were cleaned in xylene, incubate in 1% aqueous thioflavin-S for 8 minutes at room temperature then washed in 80% ethanol.

Immunohistochemistry

Slides with 20 μm thick sections were dried on warmer (50° C.) for 30 min. The sections were then equilibrated by dipping the slides in 1× PBST/TBST (here Triton X 100 is 0.1%) for 20 min at 25° C. The sections were then incubated with 0.03% hydrogen peroxide in 100% methanol for 30 min at 25° C. Following incubation, the slides were washed with 1× PBST around 4 times of 5 min per wash. Thereafter, sections were blocked with 5% BSA in PBS for 4 hrs followed by 3 washes of 5 min each with 1× PBST/TBST. The slides were incubated overnight in primary antibody (dilution 1:100) at 4° C. After washing again for 3 times with 1× PBST, the slides were incubated with fluorescently labelled secondary antibody (dilution 1:500) for 1 hr at RT. After that, sections were washed 3-4 times with 1× PBST followed by one wash with 1× PBS. Sections were covered with fluoromount and coverslips and viewed under fluorescent microscope.

Tricine Gel-Electrophoresis

100 μg of the total brain protein was loaded on the 16.5% tricine gel and ran using the cathode and anode buffer to resolve the 4.5 KD band of the Aβ42. Brain lysate was transferred to a 0.2 μM pore sized nitrocellulose membrane and probed with the mouse monoclonal antibody for the β-amyloid (SC 58508).

ELISA

Total Aβ42 (soluble+insoluble) in the brain homogenate was quantitated using the invitrogen sandwich ELISA kit (KHB 3441) with the standard provided. Strictly following the manufacturer protocol of the product.

Acetylcholine Level

50 μg of the total brain protein was used to check the level of the acetylcholine and the activity of the acetylcholinase (data not shown). Acetylcholine assay kit from thermofisher (A12217) was used strictly following the manufacturer protocol.

Immunoblotting

Protein samples run on SDS-PAGE, were transferred on PVDF or nitrocellulose membranes using wet transfer apparatus at constant current of 80 mA for 2 hrs. Ponceau S staining (0.5% w/v in 0.1% acetic acid) was used to confirm the transfer. The membrane was rinsed in 1× PBST to remove the Ponceau S stain. Having done that, the membrane was blocked for 2 hrs with either 5% non-fat skimmed milk or 5% BSA prepared in 1× PBST. After blocking, the membrane was incubated overnight at 4° C. with appropriate dilution of primary antibody in 1× PBST.

Following incubation, the membrane was washed three times for 5 min each with 1× PBST and then incubated with HRP-conjugated appropriate secondary antibody at required dilution for 1 hr. Similar washings were again carried out as after primary antibody incubation and the protein was detected by a chemiluminicent substrate kit. For re-probing a blot with different antibody, the blot was first stripped with western blot stripping solution for 15 min at 37° C. and washed thrice with 1× PBST. Thereafter, all the steps are same as mentioned above.

Transfection

Transfection in HT-22 Cells: Transfections were carried out using Lipofectamine LTX plus reagent, using manufacturer's protocol. Briefly, cells were plated in 6 well plates. When cell confluency was 70-80%, cells were transfected with optimized concentrations of plasmid. Solution A was prepared with Opti-MEM or incomplete media to which plasmids are added at a concentration of 250 µl/well. Solution B was prepared by again mixing 250 µl/well OptiMem or incomplete media, but this time with required amount of Lipofectamine LTX plus reagent and was allowed to stand at room temperature for 5 min. Solution B was then added to Solution A, mixed and incubated at room temperature for 20 min. In the meantime, media was carefully removed from the wells and 2 ml/well of Opti-MEM or Serum free media was gently added. Lastly the cocktail (A+B) was added to respective wells and the culture was incubated at 37° C. in humified incubator with 5% $CO_2$. Media was replaced with complete normal growth media after 6 hrs. Cells were left to grow for required time period (36 hrs) after which the lysates were prepared in respective lysis solutions.

Preparation of Cell Lysates

After removal of culture media the plates that were kept on ice. Thereafter cells were washed with ice-cold 1× PBS. 70 µl of ice-cold lysis buffer was added to each well and left for 15 min. The cells were scraped with a cell scraper and lysates were collected onto fresh microcentrifuge tubes. The tubes were centrifuged at 12,000 g for 25 min at 4° C. The supernatant was used fresh or stored at −70° C. for further use.

11. Sg001 Induce Downregulation of GSK3 in Time Dependent Manner in Neuronal and Non-Neuronal Cell Line The generation of the several GSK3 overexpressing mouse model have demonstrated the AD like symptoms in the animals with the NFTs and amyloid deposition, while the conditional knockout of the GSK3l3 show the normal tau protein with the normal cognition and the memory.

The level of GSK3a & B protein as well as gene transcript were found downregulated in the SG001 treated HT-22, N2A, and HEK-293 cell line with time (FIG. 1A-1C). No change in protein level was observed in the presence of proteosomal and autophagy pathways inhibitors (FIG. 1B-1C). This indicates that either transcription or translation of GSK3 in effected. The quantitation of mRNA level of GSK3 a & b at 15-20 h of Sg001 treatment showed significantly decrease in the mRNA level (FIG. 1D). The results demonstrate that the SG001 is a suppressor of the GSK-3α & β under normal condition in these cell line.

Total GSK-3reduced upon treatment with SG001 in the APP (Sweden+Indiana) overexpressing HT-22 cell line model of AD The AD condition was mimicked in the cell line model, human APP (Sweden+Indiana) was overexpressed in the mouse hippocampal cell (HT-22).

2. Cells were treated with the SG001 and the level of GSK-3 (α+β) was demonstrated at the various time intervals. Total GSK-3 also went down with the time in the SG001 treated samples. The result support that this SG001 compound is a suppressor of the total GSK-3, as shown earlier. Further, it was also cleared that the SG001 retain its GSK-3 suppressor potential in the APP (Sweden+Indiana) overexpressing condition (FIGS. 2A-2B).

3. SG001 induces degradatory pathways: The treatment with SG001 has increased autophagy and proteosomal degradatory pathaways in neuronal cell line. Treatment of SG001 has increased the level of autophagy (FIGS. 3A-3B) and the proteosomal degradatory (FIG. 3C) pathways in cells.

4. SG001 Crosses Blood Brain Barrier

The compound studied was able to cross the blood brain barrier as it was detectable in the treated animals CSF (FIG. 4).

5. Pharmacokinetics of SG001:

The rats were randomly divided into two groups (I and II) in half respectively male and female. A dose of 15 µg/kg of Compound Y was administered to group I and II. Serial blood samples (0.5 mL) were collected into heparinized tubes from the retro-orbital region at 1, 2, 4, 6, 12, 24, 36, 48, and 72 h. Samples were immediately centrifuged at 12,000 rpm for 10 min and stored at −20° C. until analysis. Plasma was processed for HPLC analysis. 100 µl Acetonitrile was added in 100 µl plasma (1:1) and centrifuge at 12,000 for 5 minute. Supernatant transferred in a clean tube. Dried under Nitrogen gas 200 µl Acetonitrile: water (1:1) was added in dry tube and centrifuge at 12,000 rpm for 15 minute. Filtered with 0.2 µm membrane filter. 20 µl samples were used for analysis in HPLC. The phannacokinetic studies has shown $T_{max}$ 48 h and $C_{max}$ 27 nM. (FIG. 5)

6. Cytotoxocity Test:

The cytotoxicity of compound SG001 in two neuronal cell lines viz; SHSY5Y and HT22 was evaluated. SH-SY5Y is a widely used neuroblastoma adrenergic cell line, which express the dopamine and other neuronal markers. Another cell line used was the HT-22, which is derived from the parent HT-4 cell line. The HT-22 cells are cholinergic hippocampal cell model and widely used to study the Alzheimer's disease. Cells were treated with 0.5 µM to the 50 µM of the compound for 24-48 h. No toxic effect of the compound at any of the dose used (FIG. 6). In-vitro studies results of the SG001 makes this compound worthy to study in the in-vivo system and hence 5× FAD mouse model of AD was chosen for the further study.

7. SG001 has preventive and therapeutic efficacy. SG001 treated animals showed improvement in the cognition decline and the memory in the behavioural assessments:

Exploratory Behavioural Test

The exploratory behaviour of the rodents is a novelty seeking activity, which do not have any relation with the need or incentive. Exploratory behaviour is also considered to be the under a strong selective pressure with the course of evolution in the rodents.

Aβ aggregate can cause the anatomical changes in the hippocampus of the brain such as the atrophy of the CA3 apical dendrites and in the severe condition death of the whole hippocampal neurons from the CA1 to the CA3. Hippocampus has been implicated as an important region of the brain in determining the normal behavioural of the mouse including the exploratory behaviour. Any manipulation in the hippocampus structure may leads to the abnormal behaviour of the animal. The Y-maze exploratory behaviour test is the measure of the damage in the hippocampus and used widely.

A significant improvement in both the treatment groups (Preventive and therapeutic), when compared with the vehicle control was observed (FIG. 6). The performance of the animals in both preventive and therapeutic treatment groups in the Y-maze exploratory behaviour tests was similar to the performance of the wild type animals (FIG. 7A). The data suggest, the compound has prevented the progression of the disease pathogenesis and memory deficit effectively. While in case of the therapeutic treatment of the compound, it was able to restore the cognitive decline and behavioural deficits. Which is a symbol of the nonnal functioning of hippocampal neurons and hence the performance of the animals Y-Maze Percent Alteration Test:

Y-maze spontaneous alteration test is a behaviour test for the measurement of spatial learning and memory. The rodents generally have the tendency to travel a new arm each time, rather than returning to the recently visited arm. Various parts of the brain are involved in this task, such as hippocampus, septum, basal forebrain, and prefrontal cortex. Thus, the performance of the rodents in this test is a reflection of the working condition of the various brain parts mainly hippocampus and the cortex.

The data of the Y-maze percent alteration test support the finding of the exploratory behavioural test. The percent alteration in, both the treatment groups (preventive and therapeutic) were found significantly higher than the vehicle control (FIG. 7B). Data support the effect of the compound to ameliorate the cognition decline and the behavioural deficit in the treated animals. The performance of the preventive group was found to be slightly better than the therapeutic group, suggesting the preventive effect of the compound more pronounced, which can be explained by the administration of the compound at the age, when little damage was done is easy to be restored.

Novel Object Test:

The advancement in the behavioural study leads to the development in the relation between the novelty and the behaviour. Novelty is such an alteration from expected likelihood of an event on the basis of both previous information and internal estimates of conditional probabilities. Novelty is a stimulus, which can change the behaviour of the animal provoked stress responses, elicit approach behaviour. Novel object test is a simple behavioural assays of memory that rely primarily on a rodent's innate exploratory behaviour in the absence of externally applied rules or reinforcement. Novel object test is widely accepted for the investigation of the alteration in the memory. Apart from the measurement of working memory, it is also used for the measurement of attention, anxiety, and preference for novelty in rodents. A normal animal tends to explore the novel object more keenly than the familiar object. The damage to the hippocampus is the only and required condition known for the poor recognition of the novel object in the test. The lesion, change in the integrity of the cells of hippocampus or the atrophy of the hippocampal area, which might be the consequences of the Aβ42 aggregation, leads to the under performance of the animals.

It was found the improved memory in the treatment groups (preventive and therapeutic). The data (FIG. 7C) support the previous finding of the exploratory behaviour and the percent alteration test. Test is the measure of the working memory of the rodent and hence the healthiness of the hippocampus area responsible for this.

Behavioural assessments of the 5× FAD mouse after the SG001 preventive and therapeutic treatments: A) Exploratory behaviour test: A significant improvement in the exploratory behaviour of the SG001 treated animals was observed (B) Percent alteration in the Y-Maze: Significant improvement in the Y-maze alteration test was calculated, the SG001 treated animals showed improved results which indicate the restoration in the spatial learning and memory (C) Novel object test: Animals treated with the SG001 performed significantly improved in the novel object test, demonstrate the improvement in the memory.

8. Morris Water Maze Test:

The water maze task was developed by the Richard Morris, to assess the spatial learning and the memory of the animals. After that it was altered in several ways to investigate the working memory, reference memory and task strategy. The Morris water maze test (MWM), is specific for the evaluation of the hippocampus, which is involved directly in the spatial learning and the memory. It is a well-established fact that the hippocampus is involved in the formation of the spatial learning and the memory, but the neuronal mechanism involved in such events is unclear. The formation of such learning and the memory may involve the other parts of the brain constituting a functionally integrated neural network.

The MWM experiment data shows the significant quick learning ability among the treatment groups (preventive and therapeutic) as compared to the vehicle control group. Within the treatment groups, the animals of preventive group were found performing better than the animals of therapeutic group (FIG. 8). The overall improvement in the behavioural of the treatment group animals strongly support the compound can ameliorate the AD pathology in the vivo animal model of the disease. FIG. 8A shows escape latency and FIG. 8B shows track diagram of MWM.

Behavioural assessments of the 5× FAD mouse after the SG001 preventive and therapeutic treatments Morris water maze(MWM): An improved performance in finding the hidden platform in the MWM was observed, which indicate the restoration in the working memory of the animals. All the behavioural assessments support the amelioration in the AD pathology.

9. Reduces the GSK3 Level in the Brain

Figure 9B:
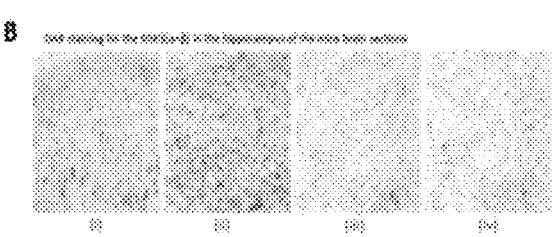
Figure 9C:
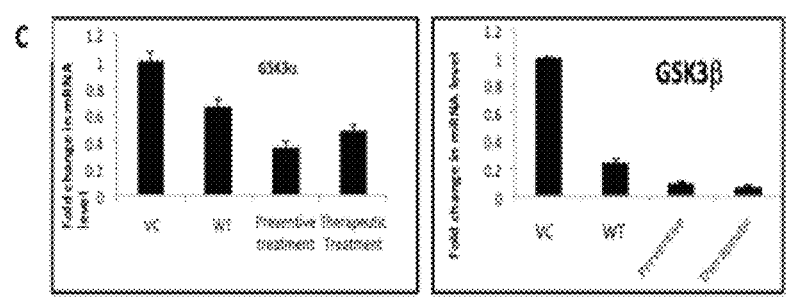
Figure 9D:
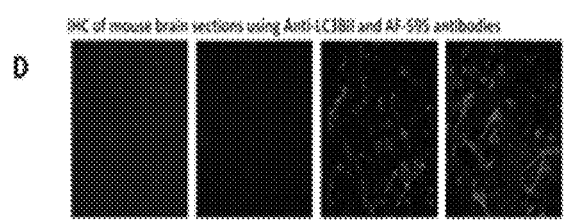

After the validation of the SG001 as the GSK-3 suppressor in the cell line, animal model 5×FAD mice were used to check whether it retained its ability or not. The hippocampal total lysate was used for the immunoblotting and significant downregulation of the GSK-3α was found in the SG001 treated animals (FIG. 9A). Further, the transcript level of both the GSK3α&β were also significantly reduced. To further validate the finding, the immunohistochemistry of the brain sections for the GSK-3 in the hippocampal region were done. Again, the total GSK-3 was found downregulated in the hippocampal region of the SG001 treated animals (FIG. 9B). Next the level of mRNA of GSK3 a&b were also decreased significantly (FIG. 9C).

The autophagy was also checked in the brain sections of the animals using the LC3B-II as the marker. A significant increase in the autophagy was observed in both the treated groups (FIG. 9D), which may be contributing in the ameliorated AD pathology in the SG001 treated animals.

So, apart from being an efficient Aβ42 aggregation inhibitor and the Aβ aggregate disruptor the SG001 also has the property to suppress the GSK-3 in the brain. A drastic improvement in the overall behaviour assessments and the overall histopathology of the brain can be explained by the SG001 autophagy induced degradation of Ab-42 plaque and GSK3 and no side effects.

10. G001 Ameliorates Hallmarks of Alzheimer's Disease

SG001 reduced the overall histopathological hallmarks significantly in the 5× FAD model. Silver staining of the brain sections of SG001 treated animals showed significant reduced plaque in size and frequency Amyloid plaque and the neurofibrillary tangles are the hallmarks of the AD and silver staining can display both the hallmarks. However, the exact mechanism of the silver staining is still not clear and according to the most accepted hypothesis, the single and short chains of amino acids are known to form the complexes with the silver and the other metal ions. In the normal tissue, where the proteins are intact these amino acids are not assessable to the silver ion and do not give the colour, but the protein aggregates have the abnormal misfolded protein, where silver ions have the plenty of chances to interact with such amino acids and give the characteristic colour.

It was found the bigger plaque deposition in the cortex and the hippocampal area of the brain in the vehicle control group, while the frequency and the size of the plaque was significantly less in both the treatment groups. The wild type brain section was also used to serve as the negative control, where no plaque like structures was seen. Further, as expected within the treatment groups the preventive treatment animals shows the better condition as compared to the therapeutic treatment group (FIG. 10A). The results of the silver staining correlate with the results of the behavioural assessment (FIG. 10A).

Thioflavin-S staining of the brain section showed the significant decrease in the amyloid deposition in the hippocampus region of the brain of SG001 treated animals Thioflavin-S has no fluorescence as such but when it binds to amyloid the intensity increases drastically. Further studies shows that the binding of the thioflavin-S is highly specific to the amyloid β-sheet structure, these properties make the thioflavin-S a powerful tool for the detection of the amyloid deposits in the brain sections.

Large and dense plaque distributed all over in the hippocampus area in the vehicle control group of the animals were observed. While the size and the distribution of the amyloid plaque in both the treated groups were significantly reduced (FIG. 10B). The data of the thioflavin-S staining support the findings of the silver staining. These clearly suggest that the treatment with the compound has significantly reduced the amyloid burden in the brain of both the preventive and therapeutic group of animals.

Immunohistochemistry of the Brain Sections for the Aβ42 Shows Significantly Reduced Amyloid Plaque in the Hippocampus and the Cortex Region Unlike the silver and the thioflavin-S staining which non-specifically stains all protein aggregates, the use of antibodies specific to the Aβ42 peptide in immunohistochemistry give the specific signals for Aβ42.

The amyloid depositions were very prominent in the hippocampus and cortex region of the brain of the diseased animals (vehicle control). Within the hippocampus, CA1 and dentate gyrus were highly loaded with the amyloid plaque in the disease control group. In contrast the amyloid burden was not only significantly reduced but the observed plaques were also smaller in size in both the treatment groups (FIG. 10C). The amyloid burden in the cortex region of the brain of the disease control was very high which explain the cognitive decline and the behavioural deficits found during the behavioural assessments of the vehicle control group of animals, while the reduced amyloid burden in the treated groups explained the significant reduced cognitive decline and the memory deficit in the brain of the preventive and therapeutic treatment groups of animals. Further, it can be inferred that the treatment of the compound reduced the amyloid burden in the whole brain irrespective of the region.

Total Aβ42 Level was Found Reduced in the Tricine-Gel Electrophoresis in the SG001 Treated Animal Groups:

Immunohistochemistry and the histological analysis showed the insoluble aggregates of the Aβ42 or the level of the Aβ42. While the whole brain homogenate consist of all types of the Aβ42 species including the monomers and oligomers. Western blot of the whole brain lysate shows the low level of the total (soluble+soluble oligomers) Aβ42 in the treatment groups, when compared with the vehicle control (FIG. 10D). AD is the consequence of the disturbance in the equilibrium of the Aβ42 production, transportation and the degradation. These results suggest the reduction in the overall Aβ42 production and not only the formation of Aβ42 aggregates as revealed by the immunohistochemistry of the brain sections and also shown by the in-vitro studies.

11. Total Aβ42 was Found Reduced in the SG001 Treated Brain Homogenates as Quantified by the Sandwich ELISA The average amount of the soluble Aβ42 peptide in the total brain homogenate of the vehicle control group was found about 1200±100 ng/mg of the total protein present in the brain homogenate, while it was about 500±50 ng/mg for the preventive group and 780±50 ng/mg for the therapeutic treatment group (FIG. 11A). The immunohistochemistry showed reduced insoluble amyloid and the brain lysate also showed significantly reduced amount of the Aβ42. This indicates that in the treatment groups total Aβ42 level in the brain is drastically reduced. This could be due to decreased production or increased degradation or increased transportation of the Aβ42 in the brain of the both treatment groups; this will be discussed in detailed in the coming section. This also supports the anti-aggregation and the aggregation disruption properties of the compound in the in-vivo system. The level of total Tau protein in the brain homogenates was significantly reduced in the treated animals Tau-hyperphosphorylation and its aggregation is the second most accepted hypothesis after the Aβ amyloid hypothesis of the AD. Some report claims that the hyperphosphorylation of the tau protein is a consequence of the Aβ42 production.

In the animal disease model (5×FAD), mutation in the APP and the PSEN1 are responsible for the establishment of the AD. But the hyperphosphorylation in the tau-protein is well established in this model of AD. Hyperphosphorylation of the tau forms the aggregates called neurofibrillary tangles, which are resistance to the SDS, and can be seen in the immunoblot. Large size aggregates in the immunoblot for the vehicle control and the aggregates were reduced in the treatment groups were found (FIG. 11B).

Acetylcholine Level in the Brain of SG001 Treated Animals was Found Restored

Acetylcholine is the main neurotransmitter for the cholinergic neurons in the brain and emerging evidence support the involvement of the acetylcholine in the memory and the cognition. The reduction in the level of acetylcholine leads to the disassociation of the inter-neuronal connection which may leads to the degeneration of the neurons. The level of the acetylcholine is reduced in the AD and the activity of acetylcholinesterase is found elevated in the AD. Numbers of the acetylcholinesterase inhibitors have been proposed for the treatment of AD.

A significantly reduced level of the acetylcholine was found in the brain of the disease control animals, while the level of the acetylcholine was restored in both the treatment groups (FIG. 11C). The acetylcholinesterase inhibition property of the compound was further checked, but significant inhibition of the activity was not found even at the higher dose. These results suggest the overall improved condition of the brain and reduction in the pathological markers.

Expression of PCNA and the Morphology of Astrocytes were Restored in the SG001 Treated Animals Biochemical and the histopathological studies on the brain of the AD patients have revealed the activation of the inflammatory pathways in the disease. Microglials are the primary immune cells of the brain, which activated in response to the lesions, neurodegenerative diseases, stroke, and brain tumours. Microglial cells in the brain are considered to be the macrophages of the brain and participating in the inflammatory responses. After the activation, these cells secrete several types of cytokines IL-1β, IL-6, TNF-α, and interferon γ (INF-γ), chemokines such as macrophage inflammatory protein 1α (MIP1α), MIP1β, CXCL8, RANTES, and monocyte chemotactic protein 1 (MCP1) and growth factors such as macrophage colony stimulating factor. The PCNA (Proliferating cell nuclear antigen) was used as the marker to check the proliferation and the activation of the microglia in the brain sections and high expression of the PCNA in the diseased brain was found. The expression of the PCNA was significantly reduced in the SG001 treated animals (FIG. 11D).

Astrocytes in the CNS performs the numerous functions such as assisting in neurogenesis, determining the micro-architecture of the grey matter, defence and maintain the homeostasis of the brain. GFAP (Glial fibrillary acidic protein) is expressed mainly by the astrocytes in the CNS, to see the morphology of the astrocytes, IHC was done using the primary antibody against the GFAP and Alexa flour 488 tagged secondary antibody. I observed distortion in the morphology and the atrophy in the AD control as expected, while astrocytes maintained the morphology and the integrity in the treated groups of the animals (FIG. 11E).

We claim:

1. A method for treating a GSK-3 mediated disease, comprising:

administering, to a subject, a compound of formula I

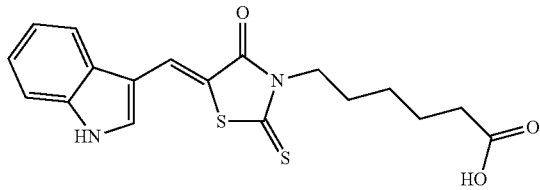

or its pharmaceutically acceptable salts, where the compound is 6-(5-ethylidene-4-oxo-2thioxo-thiazolidin-3-yl)-hexanoic acid with 1H-indole; and determining, based on the administration of the compound of formula I, a modulation of GSK-3 activity of the subject, wherein the GSK-3 mediated disease is selected from any one or more chronic neurodegenerative diseases of Alzheimer's disease, psychiatric disorders, metabolic disorders or cancer, and wherein the modulation includes downregulation of the GSK-3 activity.

2. The method of claim 1 for use in regenerative medicine.

* * * * *